US011278590B2

(12) United States Patent
Ray, II

(10) Patent No.: US 11,278,590 B2
(45) Date of Patent: Mar. 22, 2022

(54) COMPOSITIONS AND METHODS FOR TREATING NAIL INFECTIONS

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

(*) Notice: Subject to any disclaimer, the term of this patent is extended or adjusted under 35 U.S.C. 154(b) by 0 days.

(21) Appl. No.: 15/976,579

(22) Filed: May 10, 2018

(65) Prior Publication Data

US 2018/0256675 A1 Sep. 13, 2018

Related U.S. Application Data

(63) Continuation-in-part of application No. 14/990,168, filed on Jan. 7, 2016, now Pat. No. 10,898,455, and a continuation-in-part of application No. 15/597,936, filed on May 17, 2017, now Pat. No. 10,105,342, and a continuation-in-part of application No. 15/668,184, filed on Aug. 3, 2017, said application No. 15/597,936 is a continuation-in-part of application No. 15/440,800, filed on Feb. 23, 2017, now abandoned, and a continuation-in-part of application No. 14/975,172, filed on Dec. 18, 2015, now Pat. No. 9,707,229, and a continuation-in-part of application No. 14/819,342, filed on Aug. 5, 2015, now Pat. No. 10,973,804.

(60) Provisional application No. 62/298,994, filed on Feb. 23, 2016, provisional application No. 62/298,991, filed on Feb. 23, 2016, provisional application No. 62/370,571, filed on Aug. 3, 2016.

(51) Int. Cl.

| A61K 38/12 | (2006.01) |
|---|---|
| A61K 9/00 | (2006.01) |
| A61K 31/17 | (2006.01) |
| A61K 47/20 | (2006.01) |
| A61K 31/546 | (2006.01) |
| A61K 31/7036 | (2006.01) |
| A61K 31/351 | (2006.01) |
| A61K 31/496 | (2006.01) |
| A61K 31/506 | (2006.01) |
| A61K 31/196 | (2006.01) |
| A61P 31/00 | (2006.01) |
| A61P 17/00 | (2006.01) |

(52) U.S. Cl.
CPC ............ *A61K 38/12* (2013.01); *A61K 9/0014* (2013.01); *A61K 31/17* (2013.01); *A61K 31/196* (2013.01); *A61K 31/351* (2013.01); *A61K 31/496* (2013.01); *A61K 31/506* (2013.01); *A61K 31/546* (2013.01); *A61K 31/7036* (2013.01); *A61K 47/20* (2013.01); *A61P 17/00* (2018.01); *A61P 31/00* (2018.01)

(58) Field of Classification Search
CPC .... A61K 38/12; A61K 31/506; A61K 31/546; A61K 31/7036; A61K 31/351; A61K 31/496; A61K 31/196; A61K 31/17; A61K 47/20; A61K 9/0014; A61P 17/00; A61P 31/00
See application file for complete search history.

(56) References Cited

U.S. PATENT DOCUMENTS

| 4,296,104 | A | * | 10/1981 | Herschler | ................ A61K 8/42 424/679 |
|---|---|---|---|---|---|
| 5,324,746 | A | | 6/1994 | McKee et al. | |
| 6,143,794 | A | | 11/2000 | Chaudhuri et al. | |
| 6,365,635 | B1 | | 4/2002 | Nomura | |
| 9,078,853 | B2 | | 7/2015 | Ray | |
| 9,707,229 | B2 | | 7/2017 | Ray | |
| 9,717,748 | B2 | | 8/2017 | Ray | |
| 2002/0061281 | A1 | | 5/2002 | Osbakken et al. | |
| 2003/0091519 | A1 | * | 5/2003 | Zatz | ..................... A61K 9/0014 424/61 |
| 2003/0143162 | A1 | | 7/2003 | Speirs et al. | |
| 2003/0226201 | A1 | | 12/2003 | Leung et al. | |
| 2004/0033963 | A1 | | 2/2004 | Yu et al. | |
| 2004/0191329 | A1 | * | 9/2004 | Burrell | ..................... A61K 8/19 424/618 |
| 2005/0043251 | A1 | | 2/2005 | Lane | |
| 2005/0137164 | A1 | * | 6/2005 | Arkin | ................... A61K 9/0014 514/54 |
| 2005/0255048 | A1 | | 11/2005 | Hirsh et al. | |
| 2006/0246098 | A1 | | 11/2006 | Rao et al. | |
| 2008/0299060 | A1 | * | 12/2008 | Bruno | .................. A61K 9/7007 424/61 |
| 2009/0016990 | A1 | | 1/2009 | Alberte et al. | |

(Continued)

FOREIGN PATENT DOCUMENTS

| JP | H0774144 | 8/1995 |
|---|---|---|
| WO | 2006060027 | 6/2006 |

OTHER PUBLICATIONS

Bae et al., Green Nail Syndrome Treated with the Applicatin of Tobramycin Eye Drop, 2014, Ann Dermatology, vol. 26, No. 4, pp. 514-516. (Year: 2014).*
Angamuthu et al., Controlled-release injectable containing Terbinafine/PLGA microspheres for Onychomycosis Treatment, 2014, Journal of Pharmaceutical Sciences, vol. 103, pp. 1178-1183. (Year: 2014).*
Rocephin (ceftriaxone injection)Product Sheet, Galaxy Container, 2004, Roche Pharmaceuticals, 2 pages. (Year: 2004).*
Medinvent, "The NasoNeb Nasal Nebulizer", Nov. 15, 2013.

(Continued)

*Primary Examiner* — John Pak
*Assistant Examiner* — Andriae M Holt
(74) *Attorney, Agent, or Firm* — Akerman LLP

(57) ABSTRACT

A method of treating bacterial or fungal nail infections may include mixing an antibiotic or antifungal injectable medication and a diluent to formulate a topical nail composition. The topical nail composition may be administered directly to a nail affected by the bacterial or fungal infection.

17 Claims, No Drawings

(56) References Cited

U.S. PATENT DOCUMENTS

| | | |
|---|---|---|
| 2009/0123537 A1* | 5/2009 | DeBrouse ............ A61K 9/1611 424/463 |
| 2010/0081669 A1 | 4/2010 | Yang et al. |
| 2011/0105448 A1* | 5/2011 | Dhuppad ............ A61K 9/0014 514/171 |
| 2012/0157536 A1* | 6/2012 | Shah ................... A61K 9/7015 514/567 |
| 2012/0328671 A1 | 12/2012 | O'Neil et al. |
| 2013/0072563 A1 | 3/2013 | Ho |
| 2014/0256826 A1 | 9/2014 | Lemire et al. |
| 2017/0035736 A1 | 2/2017 | Ray |
| 2017/0196823 A1 | 7/2017 | Ray |
| 2017/0239277 A1 | 8/2017 | Ray |
| 2017/0246140 A1 | 8/2017 | Ray |
| 2018/0036227 A1 | 2/2018 | Ray |

OTHER PUBLICATIONS

Sutherland et al., "Antimicrobial Agents and Chemotherapy," 1985, vol. 27, pp. 495-498.

Balzarini et al., "Lancet", 2007, vol. 369, pp. 787-797.

Allen US Pharm., 2011, vol. 36(6), pp. 44-45.

Lewandowksi et al., "Military Medicine", 2013, vol. 178, pp. e503-e507.

BACTROBAN® Ointment (mupirocin ointment, 2%) Prescribing Information, GlaxoSmithKline, Revised May 2014 (17 pages).

ATICLATE® (Doxycycline Hyclate Tablets), Final Labeling Text, Aqua Pharmaceuticals, Revised Jul. 2014 (18 pages).

Ketoconazole Human Prescription Drug Label; Physician's Desk Reference, Ver. 1—Published Feb. 2007 (5 pages).

Tobramycin Human Prescription Drug Label; Physician's Desk Reference, Ver. 1—Published May 2014 (9 pages).

Ciprofloxacin Human Prescription Drug Label; Physician's Desk Reference, Ver. 1—Published Feb. 2010 (19 pages) (hereinafter Ciprofloxacin PDR).

Pan et al. Urea: a comprehensive review of the clinical literature. Dermatology Online Journal, 19(11), Nov. 2013. doj_20392. Retrieved from: http://escholarship.org/uc/item/11x463rp.

Shah, "Urea ointment (40%)," Indian J Dermatol Venereol Leprol, 69:421-422, Nov. 25, 2015. Retrieved from http://www.ijdvl.com/text.asp?2003/69/6/421/663.

Taro Pharmaceuticals U.S.A., Inc., "U-CORT-hydrocortisone acetate cream," Mar. 2012, document of 6 pages.

PCCA, "Technical Report: Spira-Wash Gel™ Wound Care Base—an Antimicrobial Evaluation," Mar. 2014, document of 2 page.

Crown Laboratories, "REA LO 39—urea cream," Aug. 2014, document of 4 pages.

Stratus Pharmaceuticals, Inc., "Remeven—urea cream," May 2011, document of 5 pages.

Medimetriks Pharmaceuticals, Inc., "Uramaxin GT—urea gel, Uramaxin GT—uramaxin gt and keradan," Apr. 2012, document of 11 pages.

Medimetriks Pharmaceuticals, Inc., "Uramaxin TS—urea cream," Apr. 2010, document of 6 pages.

Crown Laboratories, "REA LO 40—urea cream, REA LO 40—urea lotion," Aug. 2014, document of 7 pages.

Purvis, "Simultaneous High Performance Liquid Chromatography Assay of Pentoxifylline, Mupirocin, Itraconazole, and Fluticasone Propionate in Humco™ Lavare Wound Base," Chromatography 2015, 2, 642-654.

HUMCO, https://www.humco.com/pharmaceuticals/lavare/, accessed Oct. 1, 2017.

Roerig, "Diflucan-fluconazole tablet, Diflucan-fluconazole powder, for suspension," Pfizer, Mar. 2013, document of 61 pages.

PCCA, "LoxaSperse™, Powder Excipient Base for Use in Nebulization and Irrigation Compounds," 2013, document of 3 pages.

Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.

PCCA XYIFOS Trademark Appl. No. 8842712 (May 27, 2015), pp. 1-8.

Freels, Lexington Podiatry (2011), pp. 1-2.

U.S. Appl. No. 14/819,342, filed Aug. 5, 2015, Applicant is CMPD Licensing, LLC, Inventor is Jay Richard Ray, II.

Label for DIFLUCAN (Fluconazole Tablets), Distributed by Roerig, a Division of Pfizer, Mar. 2013 (35 pages).

Label (Package Insert) for Azithromycin, Distributed by SICOR Pharmaceuticals, Inc., Dec. 2016 (18 pages).

Label for BACTROBAN (mupirocin), Distributed by GlaxoSmithKline, Dec. 2015 (10 pages).

FDA Prescribing Information for NYSTATIN Powder, Distributed by Mayne Pharma, Summarized by www.drugs.com (5 pages).

PCCA, Brochure for LoxaSperse, "Powder Excipient Base for Use in Nebulization and Irrigation Compounds", 2013 (3 pages).

PCCA, "New, Exclusive PCCA Base, XyliFos™ Boost the LoxaSperse™ Power in Nasal Nebulization and Decrease your Cost", Aug. 7, 2015 (2 pages).

* cited by examiner

COMPOSITIONS AND METHODS FOR TREATING NAIL INFECTIONS

CROSS-REFERENCE TO RELATED APPLICATIONS

The present application is a continuation-in-part of U.S. patent application Ser. No. 14/990,168, filed Jan. 7, 2016, U.S. patent application Ser. No. 15/597,936, filed May 17, 2017, and U.S. patent application Ser. No. 15/668,184, filed Aug. 3, 2017, each of which is hereby incorporated herein by reference. U.S. patent application Ser. No. 15/597,936 is a continuation-in-part application of U.S. patent application Ser. No. 15/440,800, filed Feb. 23, 2017, U.S. patent application Ser. No. 14/975,172, filed Dec. 18, 2015 (now U.S. Pat. No. 9,707,229), and U.S. patent application Ser. No. 14/819,342, filed Aug. 5, 2015, each of which is hereby incorporated herein by reference. U.S. patent application Ser. No. 15/440,800 claims priority under 35 U.S.C. § 119(e) to U.S. Provisional Patent Application No. 62/298,991, filed Feb. 23, 2016, and U.S. Provisional Patent Application No. 62/298,994, filed Feb. 23, 2016, each of which is hereby incorporated herein by reference. U.S. patent application Ser. No. 15/668,184 claims priority under 35 U.S.C. § 119(e) to U.S. Provisional Patent Application No. 62/370,571, filed on Aug. 3, 2016, which is hereby incorporated herein by reference.

FIELD OF THE INVENTION

The present application relates to compounded compositions, methods of making compounded compositions, and methods of using compounded compositions to treat or prevent an infection. More specifically, the present application relates compounded topical nail compositions, methods of making compounded topical nail compositions, and methods of using compounded topical nail compositions to treat nail infections.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Nails and surrounding tissues are susceptible to many types of microbial infection. For example, bacterial nail infections include paronychia, which may also be related to viral infections. Certain fungal infections known as tinea infections are caused by mold-like fungi that thrive in warm, moist areas, thriving on the dead tissues of hair, nails, and outer skin layers. Tinea infections include tinea unguum, onychomycosis, affects the fingernails or toenails. Tinea infections are contagious and can be passed through direct contact or by contact with clothing, from shower and pool surfaces, and even from pets. Reoccurrences of nail infections are often frequent. For some subjects, such as those also diagnosed with diabetes or circulatory problems, or obese subjects, tinea infections and their treatment can be quite serious. In general, there are at least 3 different types of nail infections caused by fungi. The most common infection is frequently caused by *Trichophyton rubrum* and affects the nail bed and the area beneath the nail. Another type of infection affects only the nail surface and creates white or light colored patches. This second type of fungal infection is unusual and represents only about 10% of the reported cases. A third type of fungal infection affects the nail root and usually afflicts persons with impaired immune defense. A fourth (and unusual) type is caused by an infection of yeast fungi. Infections by yeast most often only affect nails that already are infected or damaged in some way.

The fungi are invasive to the keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Nail fungal infections are one of the hardest forms of external infection to treat, of which infections of toe nails are the most difficult to treat.

SUMMARY

In one aspect, a method of treating bacterial or fungal nail infections includes mixing an antibiotic or antifungal injectable medication and a diluent to formulate a topical nail composition and applying the topical nail composition directly to a nail affected by a bacterial or fungal infection.

In various embodiments, the antibiotic or antifungal injectable medication comprises at least one of Tobramycin for Injection, Voriconazole for Injection, Colistimethate for Injection, or Ceftriaxone for Injection. In one example, the antibiotic or antifungal injectable medication comprises at least one of Tobramycin for Injection, 1.2 g, Voriconazole for Injection, 200 mg, Colistimethate for Injection, 150 mg, or Ceftriaxone for Injection, 500 mg, and wherein the diluent is mixed in an amount between approximately 5 mL and approximately 20 mL.

In one formulation, the method may include mixing urea. The urea may be added in an amount between approximately 100 mg to approximately 1000 mg. The antibiotic or antifungal injectable medication may include at least one of Tobramycin for Injection, Voriconazole for Injection. Colistimethate for Injection, or Ceftriaxone for Injection. In one formulation, the antibiotic or antifungal injectable medication may include at least one of Tobramycin for Injection, 1.2 g, Voriconazole for Injection, 200 mg, Colistimethate for Injection, 150 mg, or Ceftriaxone for Injection, 500 mg, wherein the diluent is mixed in an amount between approximately 5 mL and approximately 20 mL.

In one formulation, the method includes mixing at least one additional active agent selected from an antibiotic, antifungal, NSAID.

In one formulation, the method may include mixing an NSAID and DMSO. The antibiotic or antifungal injectable medication may include at least one of Tobramycin for Injection, 1.2 g. Voriconazole for Injection, 200 mg, Colistimethate for Injection, 150 mg, or Ceftriaxone for Injection, 500 mg, and wherein the diluent is mixed in an amount between approximately 5 mL and approximately 20 mL.

In one formulation, the method includes mixing urea. The urea may be added in an amount between approximately 100 mg to approximately 1000 mg, and wherein the NSAID is diclofenac.

In another aspect, a method of treating a bacterial or fungal nail infection includes applying the topical nail composition directly to a nail affected by a bacterial or fungal infection wherein the topical nail composition comprises an antibiotic or antifungal injectable medication and a diluent.

In one formulation, the antibiotic or antifungal injectable medication comprises at least one of Tobramycin for Injection, Voriconazole for Injection, Colistimethate for Injection, or Ceftriaxone for Injection.

In one formulation, the antibiotic or antifungal injectable medication comprises at least one of Tobramycin for Injection, 1.2 g, Voriconazole for Injection, 200 mg, Colistimethate for Injection, 150 mg, or Ceftriaxone for Injection, 500 mg, and wherein the diluent comprises between approximately 5 mL and approximately 20 mL.

In one formulation, the topical nail composition further comprises at least one additional active agent selected from an antibiotic, antifungal, NSAID.

In one formulation, the topical nail composition further comprises an NSAID and DMSO. The antibiotic or antifungal injectable medication may include at least one of Tobramycin for Injection, 1.2 g, Voriconazole for Injection, 200 mg, Colistimethate for Injection, 150 mg, or Ceftriaxone for Injection, 500 mg, and wherein the diluent is mixed in an amount between approximately 5 mL and approximately 20 mL. The topical nail composition may further include between approximately 100 mg to approximately 1000 mg urea. In one formulation, the topical nail composition includes between approximately 100 mg to approximately 1000 mg urea and the NSAID is diclofenac.

In another aspect, a method of pretreating a bacterial or fungal nail infection includes applying a solution containing a NSAID and DMSO to a nail before applying a topical antimicrobial medication comprising one or more antimicrobial agents to the nail.

The solution may contain the NSAID diclofenac. The DMSO may be present in the solution in an amount between approximately 25% and approximately 50%. In one example, the solution contains diclofenac in an amount between approximately 0.05% and 5% and DMSO in an amount between approximately 25% and approximately 50%. The topical antimicrobial medication comprising one or more antimicrobial agents may include an antibiotic or antifungal injectable medication and a diluent.

DESCRIPTION

The present disclosure describes topical nail compositions for topical application to nails to treat bacterial or fungal nail infections. The topical nail compositions may be referred to as nail lacquers for direct application to the nail tissue. The nail lacquers may include one or more antimicrobial agents formulated for topical application to nail tissue. In some embodiments, a nail lacquer may include additives such as thickening agents, plasticizers, polymers, volatile organic compounds, or other additives to promote effective localization of the medication following application. In some embodiments, a nail lacquer may comprise a solution, suspension, or mixture lacking traditional lacquer additives. For example, nail lacquers may comprise an aqueous solution, suspension, or mixture formulated to be applied to a nail surface whereon the water carrier evaporates or is absorbed. In some embodiments, the nail lacquer may comprise a cream, lotion, gel, or ointment.

In various embodiments, the topical nail composition, which may also be referred to as a nail lacquer for topical application directly to nails, to treat of a bacterial or fungal nail infection comprises one or more antimicrobial agents and a diluent.

The antimicrobial agent may include one or more antibacterial agents, antifungal agents, antiviral agents, such as pharmaceutical drug antibiotics, antifungals, and antivirals, or combinations thereof.

In various embodiments, the topical nail composition comprises an antibacterial agent, alone or in combination with one or more antifungal agents, comprising one or more enicillins, cephalosporins, fluoroquinolones, aminoglycosides, monobactams, carbapenems, macrolides, and other antibacterials. For example, the antibacterial agent may include one or more antibacterials selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cetfoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the antibacterial agent is selected from mupirocin, gentamycin, tobrarycin, or combinations thereof. In one embodiment, the antibacterial agent includes an aminoglycoside.

In various embodiments, the topical nail composition may comprise between 0.01% and 20% by weight antibacterial agent, such as between approximately 0.01% and approximately 5%, between approximately 0.01% and approximately 3%, between approximately 0.01% and approximately 1%, between approximately 0.01% and approximately 0.25%, between approximately 0.01% and approximately 0.15%, or between approximately 0.05% and approximately 0.15%, between 0.1% and 10% by weight, between approximately 0.1% and approximately 0.5%, between approximately 0.1% and approximately 0.2%, between approximately 0.2% and approximately 0.8%, between approximately 0.2% and approximately 0.6%, between approximately 0.2% and approximately 0.4%, between approximately 0.3% and approximately 1%, between approximately 0.3% and approximately 0.8%, between approximately 0.3% and approximately 0.6%, between approximately 0.4% and approximately 1%, between approximately 0.5% and approximately 1%, between approximately 0.5% and approximately 8%, between approximately 0.6% and approximately 1%, between approximately 0.6% and approximately 0.8%, between approximately 0.8% and approximately 1%, between approximately 1% and approximately 10%, between approximately 1% and approximately 8%, between approximately 1% and approximately 5%, between approximately 1% and approximately 3%, between approximately 3% and approximately 10%, between approximately 3% and approximately 8%, or between approximately 3% and approximately 5%, between 5% and 10%, between approximately 5% and approximately 8%, between approximately 6% and approximately 10%, between approximately 6% and approximately 8%, between approximately 7% and approximately 10%, between approximately 8% and approximately 10%, between approximately 10% and approximately 20%, between approximately 10% and approximately 15%, between approximately 10% and approximately 12%, between approximately 12% and approximately 15%, or between approximately 15% and approximately 20% of the topical nail composition by weight. In some embodiments, the amount of antibacterial by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical nail composition.

In various embodiments, the one or more antimicrobial agents comprises an antibacterial agent selected from one or more antibacterials comprising Vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim.

The topical nail composition may include commercially available vancomycin, such as Vancomycin Hydrochloride for Injection, USP, which is a lyophilized powder for preparing intravenous (IV) infusions. The powder may be provided in vials (e.g., bottles) containing the equivalent of 500 mg, 1 g, 5 grams, 10 grams vancomycin base. Other formats may be used, for example Vancomycin Hydrochloride USP powder for oral solution, equivalent to 3.75 g, 7.5 g or 15 g vancomycin, and diluent, which may be a flavored, e.g., grape-flavored, diluent for reconstitution; Vancomycin Intravenous Solution, e.g., vancomycin hydrochloride 5 mg/mL, sodium chloride 9 mg/mL; or Vancomycin Capsules; or bulk powder.

The topical nail composition may include commercially available ciprofloxacin, such Ciprofloxacin Hydrochloride Solution/Drops; Ciprofloxacin Hydrochloride Tablets; Ciprofloxacin Tablets, e.g., 500 mg or 100 mg; Ciprofloxacin Hydrochloride Suspension; Ciprofloxacin Injection, USP, e.g., Ciprofloxacin Injection, USP, 20 mL, 200 mg, 1% and 40 mL or 400 mg, 1%, for intravenous injection and infusion, Premix 100 mL in 5% Dextrose, 200 mg, 0.2% and 200 mL in 5% Dextrose or 400 mg, 0.2%, for intravenous infusion; or bulk powder.

The topical nail composition may include commercially available levofloxacin, such as Levofloxacin Injection, which may be supplied in single-use vials containing a concentrated solution with the equivalent of 500 mg of levofloxacin USP in 20 mL vials and 750 mg of levofloxacin USP in 30 mL vials; Levofloxacin Solution/Drops; Levofloxacin Tablet; or bulk powder.

The topical nail composition may include commercially available azithromycin, such as Azithromycin for Injection USP, which may be supplied in lyophilized form under a vacuum in a 10 mL vial equivalent to 500 mg of azithromycin for intravenous administration including sodium hydroxide and 413.6 mg citric acid; Azithromycin for Oral Suspension, USP, which may be supplied for suspension in 100 mg/5 mL or 200 mg/5 mL; Azithromycin Tablets; or bulk powder.

The topical nail composition may include commercially available clindamycin, such as Clindamycin Phosphate Cream; Clindamycin Phosphate Gel; Clindamycin Phosphate Suspension; Clindamycin Phosphate Injection Solution; Clindamycin Phosphate for Injection; or bulk powder.

The topical nail composition may include commercially available doxycycline, such as Doxycycline Hyclate tablets; Doxycycline Hyclate Tablets; Doxycycline Hyclate Pellets; Doxycycline for Suspension; Doxycycline Hyclate Powder for Suspension; or bulk powder.

The topical nail composition may include commercially available mupirocin, such as Mupirocin Ointment; Mupirocin Cream; or bulk powder.

The topical nail composition may include commercially available cefepime, such as Cefepime Hydrochloride Injection, Powder, for Solution, supplied in 500 mg, 1 g, and 2 g vials; Cefepime Hydrochloride Injection Solution; or bulk powder.

The topical nail composition may include commercially available streptomycin, such as Streptomycin for Injection USP, which may be supplied in 1 g vials; Streptomycin Injection. Powder, Lyophilized, for Solution; or bulk powder.

The topical nail composition may include commercially available sulfamethoxazole/trimethoprim, such as Sulfamethoxazole and Trimethoprim Tablets; Sulfamethoxazole and Trimethoprim Injection; Sulfamethoxazole and Trimethoprim Suspension; or bulk powder.

In various embodiments, the topical nail composition comprises an antifungal agent, alone or in combination with one or more antibacterial agents, wherein the an antifungal agent includes one or more antifungals selected from one or more categories of antifungal agents including azoles (imidazoles), antimetabolites, allylamines, morpholine, glucan synthesis inhibitors (echinocandins), polyenes, benoxaaborale; other antifungal/onychomycosis agents, and new classes of antifungal/onychomycosis agents. For example, the anti-fungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, imiconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antibacterial agent is selected from one or more azoles. In one embodiment, the antifungal agent is selected from intraconazole, voriconazole, or combination thereof.

In various embodiments, the topical nail composition may comprise between approximately 0.01% and approximately 20% by weight antifungal agent, such as between approximately 0.01% and approximately 5%, between approximately 0.01% and approximately 3%, between approximately 0.01% and approximately 1%, between approximately 0.01% and approximately 0.25%, between approximately 0.01% and approximately 0.15%, or between approximately 0.05% and approximately 0.15%, between 0.1% and 10% by weight, between approximately 0.1% and approximately 0.5%, between approximately 0.1% and approximately 0.2%, between approximately 0.2% and approximately 0.8%, between approximately 0.2% and approximately 0.6%, between approximately 0.2% and approximately 0.4%, between approximately 0.3% and approximately 1%, between approximately 0.3% and approximately 0.8%, between approximately 0.3% and approximately 0.6%, between approximately 0.4% and approximately 1%, between approximately 0.5% and approximately 1%, between approximately 0.5% and approximately 8%, between approximately 0.6% and approximately 1%, between approximately 0.6% and approximately 0.8%, between approximately 0.8% and approximately 1%, between approximately 1% and approximately 3%, between approximately 1% and approximately 10%, between approximately 1% and approximately 8%, between approximately 1% and approximately 5%, between approximately 1% and approximately 3%, between approximately 3% and approximately 10%, between approximately 3% and approximately 8%, or between approximately 3% and approximately 5%, between 5% and 10%, between approximately 5% and approximately 8%, between approximately 6% and approximately 10%, between approximately 6% and approximately 8%, between approximately 7% and approximately 10%, between approximately 8% and approximately 10%, between approximately 10% and approximately 20%, between approximately 10% and approximately 15%, between approximately 10% and approximately 12%, between approximately 12% and approximately 15%, or between approximately 15% and approximately 20% of the topical nail composition by weight. In some embodiments, the amount of antifungal by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical nail composition.

In various embodiments, the one or more antimicrobial agents comprises an antifungal agent selected from one or more antifungals comprising fluconazole, itraconazole, voriconazole, amphotericin, nystatin, clotrimazole, econazole, or ketoconazole.

The topical nail composition may include commercially available fluconazole, such as Fluconazole in Dextrose Inject, Solution; Fluconazole in Sodium Chloride Injection, Solution; Fluconazole Injection; Fluconazole Powder, for Suspension; Fluconazole Tablets; or bulk powder.

The topical nail composition may include commercially available itraconazole, such as Itraconazole Capsule; Itraconazole Injection Solution; or bulk powder.

The topical nail composition may include commercially available voriconazole, such as Voriconazole Injection, Powder, Lyophilized, for Solution; Voriconazole Injection, Powder, for Solution; Voriconazole Powder; Voriconazole Tablet; or bulk powder.

The topical nail composition may include commercially available amphotericin, such as Amphotericin B injection, Lipid Complex; Amphotericin B Injection. Powder, Lyophilized, for Solution; or bulk powder.

The topical nail composition may include commercially available nystatin, such as Nystatin Cream; Nystatin Ointment; Nystatin Powder (Topical); or bulk powder.

The topical nail composition may include commercially available clotrimazole, such as Clotrimazole Cream; Clotrimazole Lotion; Clotrimazole Liquid; Clotrimnazole Solution; or bulk powder.

The topical nail composition may include commercially available econazole, such as Econazole Nitrate Cream; Econazole Nitrate Foam; or bulk powder.

The topical nail composition may include commercially available ketoconazole, such as Ketoconazole Foam; Ketoconazole Cream; Ketoconazole Suspension; Ketoconazole Tablet; Ketoconazole Suspension Shampoo; or bulk powder.

As introduced above, in various embodiments, the antibacterial agent or one or more antibacterials thereof, the antifungal agent or one or more antifungals thereof, or combination thereof comprises a commercially available antibacterial or antifungal for injection.

In one example, the topical nail composition comprises a commercially available tobramycin as tobramycin for injection. Tobramycin for injection is commercially available in various strengths and volumes. For example, tobramycin for injection is currently available in as Tobramycin Injection, USP, 40 mg/l mL (30 mL), 1.2 g multi-dose vials, 80 mg/2 mL vials, 240 mg/6 mL, 20 mg or 80 mg in 20 mg/2 mL vials. Tobramycin for injection may be provided as powder or solution and may include tobramycin sulfate.

In any of the above or another example, the topical nail composition comprises a commercially available voriconazole as voriconazole for injection. Voriconazole for injection is commercially available in various strengths and volumes. For example, voriconazole for injection is commercially available in various strengths and volumes, for example, voriconazole for injection is currently available as Voriconazole for Injection supplied in a single dose vials as a sterile lyophilized powder equivalent to 200 mg voriconazole and 3200 mg sulfobutyl ether beta-cyclodextrin sodium (SBECD) and single doses vial as a sterile lyophilized white to off white cake or powder equivalent to 200 mg voriconazole and 3200 mg hydroxypropyl β-cyclodextrin (HPβCD).

In any of the above or another example, the topical nail composition comprises commercially available colistimethate as colistimethate for injection. Colistimethate for injection is commercially available in various strengths and volumes. For example, colistimethate for injection, USP is currently available in vials containing colistimethate sodium equivalent to 150 mg colistin base activity per vial. Colistimethate for Injection, USP, 150 mg.

In any of the above or another example, the topical nail composition comprises commercially available ceftriaxone as ceftriaxone for injection. Ceftriaxone for injection is commercially available in various strengths and volumes. For example, Ceftriaxone for injection is currently available as Ceftriaxone for Injection, USP, 500 mg, 250 mg, 2 g, and 1 g. Ceftriaxone Injection, USP, Solution is also available premixed as a frozen, iso-osmotic, sterile, nonpyrogenic solution of ceftriaxone sodium in 1 g equivalent of ceftriaxone, iso-osmotic with approximately 1.9 g Dextrose Hydrous, USP, and 2 gm equivalent of ceftriaxone, isoosmotic with approximately 1.2 g Dextrose Hydrous, USP.

In any of the above or another example, the topical nail composition comprises commercially available levofloxacin as levofloxacin for injection. Levofloxacin for injection is commercially available in various strengths and volumes. For example, levofloxacin for injection is currently available in 500 mg/20 mL strength, 20 mL volume single use container, and in 250 mg/50 mL strength, 50 mL, 100 mL, and 150 mL single-use containers.

In any of the above or another example, the topical nail composition comprises commercially available linezolid as linezolid for injection. Linezolid for injection may be supplied as a ready-to-use sterile isotonic solution for intravenous infusion. For example, each container may contain 600 mg of linezolid in 300 mL of a clear, colorless to slightly yellow aqueous solution. Inactive ingredients may include: citric acid anhydrous USP 1.92 mg/mL, sodium chloride USP 9 mg/mL, sodium hydroxide NF 0.76 mg/mL, and water for injection USP. Sodium hydroxide NF and/or hydrochloric acid NF are typically used to adjust the pH. The sodium (Na+) content may be about 3.98 mg/mL (52 mEq/300-mL container). Zyvox for injection is supplied as a ready-to-use sterile isotonic solution for intravenous infusion. Each mL contains 2 mg of linezolid. Inactive ingredients are sodium citrate, citric acid, and dextrose in an aqueous vehicle for intravenous administration. The sodium (Na+) content is about 0.38 mg/mL (5 mEq per 300-mL bag; 3.3 mEq per 200-mL bag; and 1.7 mEq per 100-mL bag).

In these or other embodiments, the antibacterial agent or one or more antibacterials thereof, the antifungal agent or one or more antifungals thereof, or combination thereof comprises bulk powder, ground commercial oral tablets, a commercial oral, nasal, or injection solution or suspension, or commercially available topical cream, ointment, foam, lotion, or gel.

For example, the topical nail composition may include commercially available tobramycin in bulk powder, nasal solution, drops, or powder, ophthalmic suspension, solution, or drops, nebulizer formulas, or combination thereof. In this or another example, the topical nail composition may include voriconazole in a commercially available in bulk powder, oral suspension or powder for oral suspension, ground tablet, or combination thereof. In any of the above or another example, the topical nail composition may include linezolid in a commercially available bulk powder format, granules for oral suspension, oral solution, injection dosage, ground oral tablet, or combination thereof. In any of the above or another example, the topical nail composition may include mupirocin in a commercially available in cream, ointment, lotion, ground oral tablet, bulk powder, or combination thereof. In any of the above or another example, the topical nail composition may include itraconazole in a commercially available bulk powder, capsule, pellet, or combination thereof. In various embodiments, one or more of the antimicrobial agents may be provided in a compounded tablet comprising bulk powder, ground oral tablets, or powder for suspension or solution.

In various embodiments, the topical nail composition comprises one or more antimicrobial agents and one or more keratolitic agents selected form urea, salicylic acid, papain, or combinations thereof. For example, the topical nail composition may comprise one or more antimicrobial agents and urea. In various embodiments, the topical nail composition may comprise between approximately 1% and approximately 30% by weight urea, such as between approximately 1% and approximately 20%, between approximately 1% and approximately 15%, between approximately 1% and approximately 10%, between approximately 1% and approximately 8%, between approximately 1% and approximately 7%, or between approximately 1% and approximately 6%, between 1% and 5% by weight, between approximately 1% and approximately 4%, between approximately 1% and approximately 3%, between approximately 1% and approximately 2%, between approximately 2% and approximately 4%, between approximately 3% and approximately 2%, between approximately 3% and approximately 4%, between approximately 3% and approximately 5%, or between approximately 3% and approximately 7%, between approximately 3% and approximately 10%, between approximately 4% and approximately 8%, between approximately 4% and approximately 10%, between approximately 6% and approximately 8%, between approximately 6% and approximately 10%, between approximately 8% and approximately 10%, between approximately 10% and approximately 20%, between approximately 10% and approximately 15%, between approximately 15% and approximately 15%, between approximately 20% and approximately 20%, between approximately 25% and approximately 25%, between approximately 25% and approximately 30%, or between approximately 20% and approximately 30% of the topical nail composition by weight. In some embodiments, the amount of urea by weight may be approximately 1%, approximately 1.5%, approximately 1.8%, approximately 2%, approximately 2.1%, approximately 2.2%, approximately 2.3%, approximately 2.4%, approximately 2.5%, approximately 2.6%, approximately 2.7%, approximately 2.8%, approximately 2.9%, approximately 3%, approximately 3.1%, approximately 3.2%, approximately 3.3%, approximately 3.5%, approximately 3.7%, approximately 3.9%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, approximately 23%, approximately 25%, approximately 27%, approximately 29%, approximately 30% or any other percentage between approximately 1% and 30% by weight of the topical nail composition.

As introduced above, the topical nail composition may include a diluent comprising one or more diluents. The diluent may be liquid, semi-liquid, or solid. For example, the diluent may include an aqueous, organic, or inorganic solution, cream, gel, ointment, lotion, emulsion, or paste. In some embodiments, the diluent includes a carrier or vehicle composition such as a base cream, ointment, gel, lotion, foam, solution, suspension. The diluent may include lecithin, phospholipids, glycols, paraffin, fatty acids, carbopols, alcohols, lanolin, for example. In some embodiments, the diluent comprises an aqueous solution such as a saline solution. For example, the topical nail composition may comprise a diluent comprising sodium hydroxide solution, which may be a sterile solution, an alcohol, water, e.g., purified water, water for irrigation, water for injection, or a sterile water. In one embodiment, the diluent comprises a sodium chloride 0.09% solution (sterile). The diluent may be present in an amount sufficient to obtain the desired amount of active agents per unit weight or volume.

In various embodiments, the topical nail composition comprises Diluent dimethyl sulfoxide (DMSO). In some embodiments, a DMSO may be used as a diluent. A commercially available 45.5% DMSO solution, for example, may be used. Other percent concentrations of DMSO may be used, for example DMSO may be present in an amount between approximately 10% and approximately 50%, such as between approximately 15% and approximately 50%, between approximately 20% and approximately 50%, between approximately 25% and approximately 50%, between approximately 30% and approximately 50%, between approximately 35% and approximately 50%, between approximately 40% and approximately 50%, between approximately 20% and approximately 40%, or between approximately 20% and approximately 30%.

In various embodiments, the topical nail composition comprises one or more antimicrobial agents, as introduced above, and a nonsteroidal anti-inflammatory drug (NSAID) agent. In further embodiments, the topical nail composition may further include urea, as also introduced above. According to various embodiments, the NSAID agent may include one or more NSAIDS selected from oxicams, such as meloxicam and piroxicam; salicylic acid derivatives, such as aspirin, diflunisal, salsalate, and trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, and tolmetin; fenamates, such as meclofenamate; and/or COX-2 inhibitors, such as celecoxib, rofecoxib, and valdecoxib. All or a portion of the NSAID agent may be obtained from bulk powder. However, in some embodiments, all or a portion of the NSAID agent may be obtained from ground oral tablets, commercial solutions or suspensions, commercial NSAID topical creams such as creams, ointments, lotions, foams, solutions, gels, or combination thereof. For example, in one formula, the NSAID agent comprises the NSAID diclofenac obtained from a commercial diclofenac solution.

In various embodiments, the topical nail composition may comprise between approximately 0.01% and approximately 20% by weight NSAID, such as between approximately 0.01% and approximately 5%, between approximately 0.01% and approximately 3%, between approximately 0.01% and approximately 1%, between approximately 0.01% and approximately 0.25%, between approximately 0.01% and approximately 0.15%, or between approximately 0.05% and approximately 0.15%, between 0.1% and 10% by weight, between approximately 0.1% and approximately 0.5%, between approximately 0.1% and approximately 0.2%, between approximately 0.2% and approximately 0.8%, between approximately 0.2% and approximately 0.6%, between approximately 0.2% and approximately 0.4%, between approximately 0.3% and approximately 1%, between approximately 0.3% and approximately 0.8%, between approximately 0.3% and approximately 0.6%, between approximately 0.4% and approximately 1%, between approximately 0.5% and approximately 1%, between approximately 0.5% and approximately 8%, between approximately 0.6% and approximately 1%, between approximately 0.6% and approximately 0.8%, between approximately 0.8% and approximately 1%, between approximately 1% and approximately 3%, between approximately 1% and approximately 10%, between approximately 1% and approximately 8%, between approximately 1% and approximately 5%, between approximately 1% and approximately 3%, between approximately 3% and approximately 10%, between approximately 3% and approximately 8%, or between approximately 3% and approximately 5%, between 5% and 10%, between approximately 5% and approximately 8%, between approximately 6% and approximately 10%, between approximately 6% and approximately 8%, between approximately 7% and approximately 10%, between approximately 8% and approximately 10%, between approximately 10% and approximately 20%, between approximately 10% and approximately 15%, between approximately 10% and approximately 12%, between approximately 12% and approximately 15%, or between approximately 15% and approximately 20% of the topical nail composition by weight. In some embodiments, the amount of NSAID by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical nail composition.

The compounded nail composition may also include one or more additives as emollients thickening agents, plasticizers, polymers, volatile organic compounds, or other additives to promote ease of application, effective localization of the medication, or comfort following administration of the composition to a nail.

In some embodiments, a combination therapy for treatment of a fungal or nail infection includes sequential administration of the topical nail composition comprising one or more antimicrobial agents and diluent with a DMSO and NSAID composition as described herein. In one embodiment, the topical nail composition also includes urea as described herein.

In some embodiments, the NSAID is combined with DMSO and used as a nail lacquer sequentially, either before or after, with the topical nail composition including the antimicrobial, which may also include urea and/or diluent as described above and elsewhere herein. In one embodiment, the NSAID includes diclofenac. Diclofenac may be present in an amount between approximately 0.05% and approximately 5%, such as between approximately 1% and approximately 3%, between approximately 1% and approximately 2%, or approximately 1.5%. DMSO may be present in an amount between approximately 10% and approximately 50%, such as between approximately 15% and approximately 50%, between approximately 20% and approximately 50%, between approximately 25% and approximately 50%, between approximately 30% and approximately 50%, between approximately 35% and approximately 50%, between approximately 40% and approximately 50%, or between approximately 20% and approximately 40%.

Example Topical Nail Compositions

One example topical nail composition comprises an antibacterial agent comprising approximately 1.2 g of tobramycin and 20 mg mupirocin; an antifungal agent comprising approximately 50 mg itraconazole; approximately 500 mg urea; and a diluent comprising approximately 15 mL 0.09% Sterile Sodium Chloride. The composition may be applied to nails once daily or as otherwise directed, such as two or more times a day. In various embodiments, the tobramycin comprises Tobramycin for Injection, USP. The tobramycin may also include other tobramycin formats, such as those described herein. The mupirocin may include a bulk powder, ground tablets, or a commercially available mupirocin ointment or cream. The itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agents or urea agent. In various embodiments, the tobramycin may be replaced or supplemented with voriconazole, colistimethate, or ceftriaxone, such as approximately 200 mg Voriconazole for Injection, approximately 150 mg Colistimethate for Injection, or approximately 500 mg Ceftriaxone for Injection.

Another example topical nail composition comprises an antibacterial agent comprising approximately 80 mg gentamicin and approximately 20 mg mupirocin; an antifungal agent comprising approximately 50 mg itraconazole; approximately 500 mg urea; and a diluent comprising approximately 15 mL 0.09% Sterile Sodium Chloride. The composition may be applied to nails once daily or as otherwise directed, such as two or more times a day. In various embodiments, the gentamicin comprises gentamicin bulk powder, injection solution, or ointment. The mupirocin may include a bulk powder, ground tablets, or a commercially available mupirocin ointment or cream, for example. The itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agents or urea agent. In various embodiments, the gentamicin may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

Another example topical nail composition comprises an antifungal agent comprising approximately 200 mg voriconazole; approximately 500 mg urea; and a diluent comprising approximately 15 mL 0.09% Sterile Sodium Chloride. The composition may be applied to nails once daily or as otherwise directed, such as two or more times a day. In various embodiments, the voriconazole comprises gentamicin bulk powder, for injection, injection solution, ointment, or other commercially available voriconazole format. The urea may be a bulk urea powder, ointment, or cream. In various embodiments, the amount of diluent may be reduced by an amount of base carrier provided by the antimicrobial agent or urea agent. In various embodiments, the voriconazole may be replaced by tobramycin for injection, colistimethate, or ceftriaxone, such as approximately 1.2 g Tobramycin for Injection, approximately 150 mg Colistimethate for Injection, or approximately 500 mg Ceftriaxone for Injection.

Another example topical nail composition comprises an antifungal agent comprising approximately 100 mg itraconazole; approximately 500 mg urea; and a diluent comprising approximately 15 mL 0.09% Sterile Sodium Chloride. The composition may be applied to nails once daily or as otherwise directed, such as two or more times a day. In various embodiments, the itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agent or urea agent. In various embodiments, the itraconazole may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

In one embodiment, a bacterial of fungal nail infection treatment includes any of the above topical nail compositions for administration sequentially, either before or after, a topical nail infection composition comprising an NSAID agent comprising diclofenac and DMSO comprising approximately 1.5% diclofenac and approximately 45.5% DMSO.

One example topical nail composition comprises an antibacterial agent comprising approximately 1.2 g of tobramycin and approximately 20 mg mupirocin; an antifungal agent comprising approximately 50 mg itraconazole; approximately 500 mg urea; and a diluent comprising approximately 15 mL 0.09% Sterile Sodium Chloride. The topical nail composition may also comprising an NSAID agent comprising diclofenac and DMSO comprising approximately 1.5% diclofenac and approximately 45.5% DMSO. The NSAID and DMSO may be provided in a 10 mL solution. In one example, the solution of DMSO and NSAID replace all or a portion of the sodium chloride. The composition may be applied to nails once daily or as otherwise directed, such as two or more times a day. In various embodiments, the tobramycin comprises Tobramycin for Injection. USP. The tobramycin may also include other tobramycin formats, such as those described herein. The mupirocin may include a bulk powder, ground tablets, or a commercially available mupirocin ointment or cream. The itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agents, urea agent. NSAID agent, or DMSO. In various embodiments, the tobramycin may be replaced or supplemented with voriconazole, colistimethate, or ceftriaxone, such as approximately 200 mg Voriconazole for Injection, approximately 150 mg Colistimethate for Injection, or approximately 500 mg Ceftriaxone for Injection.

Another example topical nail composition comprises an antibacterial agent comprising approximately 80 mg gentamicin and approximately 20 mg mupirocin; an antifungal agent comprising approximately 50 mg itraconazole (bulk powder); approximately 500 mg urea; and a diluent comprising approximately 15 mL 0.09% Sterile Sodium Chloride. The topical nail composition may also comprising an NSAID agent comprising diclofenac and DMSO comprising approximately 1.5% diclofenac and approximately 45.5% DMSO. The NSAID and DMSO may be provided in a 10 mL solution. In one example, the solution of DMSO and NSAID replace all or a portion of the sodium chloride. The composition may be applied to nails once daily or as otherwise directed, such as two or more times a day. The composition may be applied to nails once daily or as otherwise directed, such as two or more times a day. In various embodiments, the gentamicin comprises gentamicin bulk powder, injection solution, or ointment. The mupirocin may include a bulk powder, ground tablets, or a commercially available mupirocin ointment or cream, for example. The itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agents, urea agent, NSAID agent, or DMSO. In various embodiments, the gentamicin may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

Another example topical nail composition comprises an antifungal agent comprising approximately 200 mg voriconazole; approximately 500 mg urea; and a diluent comprising approximately 15 mL 0.09% Sterile Sodium Chloride. The topical nail composition may also comprising an NSAID agent comprising diclofenac and DMSO comprising approximately 1.5% diclofenac and approximately 45.5% DMSO. The NSAID and DMSO may be provided in a 10 mL solution. In one example, the solution of DMSO and NSAID replace all or a portion of the sodium chloride. The composition may be applied to nails once daily or as otherwise directed, such as two or more times a day. The composition may be applied to nails once daily or as otherwise directed, such as two or more times a day. In various embodiments, the voriconazole comprises gentamicin bulk powder, for injection, injection solution, ointment, or other commercially available voriconazole format. The urea may be a bulk urea powder, ointment, or cream. In various embodiments, the amount of diluent may be reduced by an amount of base carrier provided by the antimicrobial agent, urea agent, NSAID agent, or DMSO. In various embodiments, the voriconazole may be replaced by tobramycin for injection, colistimethate, or ceftriaxone, such as approximately 1.2 g Tobramycin for Injection, approximately 150 mg Colistimethate for Injection, or approximately 500 mg Ceftriaxone for Injection.

Another example topical nail composition comprises an antifungal agent comprising approximately 100 mg itraconazole; approximately 500 mg urea; and a diluent comprising approximately 15 mL 0.09% Sterile Sodium Chloride. The topical nail composition may also comprising an NSAID agent comprising diclofenac and DMSO comprising approximately 1.5% diclofenac and approximately 45.5% DMSO. The NSAID and DMSO may be provided in a 10 mL solution. In one example, the solution of DMSO and NSAID replace all or a portion of the sodium chloride. The composition may be applied to nails once daily or as otherwise directed, such as two or more times a day. The composition may be applied to nails once daily or as otherwise directed, such as two or more times a day. In various embodiments, the itraconazole may be a bulk powder, capsule, ground tablet, or other commercially available itraconazole format. The urea may be a bulk urea powder, ointment, or cream. In various embodiments, the amount of diluent may be reduced by an amount of base carrier provided by the antimicrobial agent, urea agent. NSAID agent, or DMSO. In various embodiments, the itraconazole may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

Methods of Making a Topical Nail Composition

A method of making a topical nail composition may comprise combining an antimicrobial agent and diluent. Combining may include mixing the components to formulate a combined solution, suspension, mixture, or emulsion. In various embodiments, the method may include combining antimicrobial agents comprising an antibacterial agent, an antifungal agent, or both, and a diluent. The antibacterial agent may comprise one or more antibacterials, such as those described herein. The antifungal agent may comprise one or more antifungals, such as those described herein. The diluent may comprise a diluent as described herein, which may include diluent comprising carriers, which may include base vehicles, from the active agent components combined during the method. The method may include combining urea. The method may also include combining an NSAID agent. The method may also include combining DMSO.

In various embodiment, making the topical nail composition comprises encapsulating or providing one or more of the antimicrobial agents into one or more capsules. The capsules may be opened to release the contents when formulating the topical nail composition. The antimicrobial agents may be obtained from bulk powder or ground tablets. The one or more capsules may be provided in a kit for formulation with other components of the topical nail composition prior to administration. For example, a kit may include one more capsules of antimicrobial agent powders, such as commercially available bulk powders, ground oral tablets, vials containing antimicrobial powder, solution, or suspensions, which may include commercially available parenteral, injection, oral, ophthalmic, otic, or skin antimicrobial compositions; tubes or containers containing antimicrobial agent topical creams, gels, ointments, lotions, emulsions, foams, which may include commercially available parenteral, injection, oral, ophthalmic, otic, or skin antimicrobial compositions. In one example, making the topical nail composition comprises encapsulating the antimicrobial agent powders obtained from bulk powders into one or more compounded capsules comprising the amount needed or a divisible amount needed to formulate the topical nail composition. For example, in an embodiment requiring tobramycin, intraconazole, mupirocin, and urea. Making the topical nail composition may comprise encapsulating itraconazole and mupirocin bulk powders, encapsulating urea bulk powder, and providing a vial of Tobramycin for Injection. An example capsule containing itraconazole and mupirocin may include itraconazole and mupirocin in a ratio between approximately 1:20 and approximately 20:1. In one embodiment, a capsule includes mupirocin and itraconazole in a ratio of approximately 2:5. For example, a compounded capsule may include approximately 20 mg of Mupirocin USP and approximately 30 mg of Itraconazole USP Micronized. Capsules containing antimicrobial agents may also include excipients. Excipients may include dispersants, diluents, or surfactants, for example. Excipients may include xylitol or poloxamers. In one embodiment, a capsule containing antimicrobial agent powders may include PCCA LoxaSperse™. LoxaSperse™ is an excipient base powder manufactured by PCCA (Houston, Tex.) used as a chemical dispersing or solubilizing agent in irrigation or nebulization formulations, improving the solubility and dispersibility of poorly water soluble Active Pharmaceutical Ingredients (APIs) or agents. LoxaSperse is a blend of specially micronized xylitol with an optimized ratio of micronized poloxamers, designed to improve the dispersibility and solubility of APIs. In some embodiments, XyliFos™ excipient base powder comprising xylitol, poloxamer 407, hydroxylpropyl betadex, and epigallocatechin gallate may be used. LoxaSperse™, XyliFos™, or both may be used. The ratio of LoxaSperse™ or XyliFos™ to antimicrobial agent in a capsule may be approximately 20:1 and approximately 1:20. For example, in one embodiment, a capsule compounded to contain approximately 20 mg of Mupirocin USP and approximately 30 mg of Itraconazole USP Micronized, may further contain approximately 276 mg LoxaSperse™.

In one embodiment, urea may be provided in a capsule comprising urea powder. The capsule may be opened to release the contents when formulating the topical nail composition. The urea powder may be obtained from bulk urea USP powder. The capsule may include additional actives or inactives. In some embodiments, a capsule containing urea may include an excipient. Excipients may include dispersants, diluents, or surfactants, for example. Excipients may include xylitol or poloxamers. In one embodiment, a capsule containing urea may include PCCA LoxaSperse™. LoxaSpersem™ is an excipient base powder manufactured by PCCA (Houston, Tex.) used as a chemical dispersing or solubilizing agent in irrigation or nebulization formulations, improving the solubility and dispersibility of poorly water soluble Active Pharmaceutical Ingredients (APIs) or agents. LoxaSperse is a blend of specially micronized xylitol with an optimized ratio of micronized poloxamers, designed to improve the dispersibility and solubility of APIs. In some embodiments, XyliFos™ excipient base powder comprising xylitol, poloxamer 407, hydroxylpropyl betadex, and epigallocatechin gallate may be used.

In one embodiment, making the topical nail composition comprises combining urea powder with an excipient base comprising LoxaSperse™ to form the dry powder formulation. Encapsulating the dry powder may comprise encapsulating the LoxaSperse and approximately 500 mg of urea or other amount needed for the formulation, preferably in an amount that the need amount is divisible by, in the capsule. The capsule may contain LoxaSperse™ in a ratio of approximately 1:4 with respect to urea, such as approximately 131 mg in a capsule containing 500 mg urea. Other ratios may be used, e.g., between approximately 20:1 and approximately 1:20. Making the topical nail composition may further comprise obtaining the urea from a bulk source.

In some embodiments, making the topical nail composition may include providing a vial or container containing DMSO. The vial or container may also include an NSAID. For example, the vial or container may include DMSO and diclofenac. DMSO makes up approximately 45.5% of the diclofenac solution (1.5% Stock Solution). The DMSO may be included in a kit for the treatment of a fungal or bacterial nail infection. In a further example, making the topical nail composition may include providing a vial or container containing an NSAID solution or suspension. For example, diclofenac may be provided in an aqueous solution comprising a diclofenac sodium solution. In one embodiment, the diclofenac or pharmaceutically acceptable salt thereof may comprise a diclofenac sodium solution for topical application. The diclofenac sodium solution may contain, for example, 1.5% (w/w) diclofenac sodium wherein each 1 mL of solution may contain approximately 16.05 mg of diclofenac sodium. In one embodiment, the diclofenac solution comprises a diclofenac sodium solution 1.5% (w/w) such as that manufactured under the trade name PENNSAID® by Nuvo Manufacturing, Varennes, Quebec, Canada for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used. In another example, making the topical nail composition comprises encapsulating or providing a capsule containing an NSAID powder, e.g., bulk powder or ground tablet. Such vials, containers, or capsules containing DMSO, NSAID, or both may be provided in a kit for the treatment of a bacterial or fungal nail infection.

Making the topical nail composition may comprise adding the contents of one or more capsules, vials, tubes or containers containing the components of the composition and mixing to form the topical nail composition.

In one example, a method of making a topical nail composition comprises combining an antibacterial agent comprising between approximately 0.06 g and approximately 1.5 g of a first antibacterial, an antifungal agent comprising between approximately 0.01 g and approximately 1.5 g of a first antifungal, or both, and between approximately 5 mL and approximately 25 mL of a diluent. The first antibacterial or first antifungal may be any suitable antibacterial or antifungal, such as those described herein. In various embodiments, at least one of the first antibacterial or first antifungal comprises an antibacterial or antifungal for injection. It will be understood that the example formulations herein may be suitably scaled for making larger or smaller batches of topical nail composition. In some embodiments, the antibacterial agent, antifungal agent, or both may include a second antibacterial or antifungal. The second antibacterial or antifungal may be added in an amount between approximately 0.01 g and approximately 0.5 g. The second antibacterial or second antifungal may be any suitable antibacterial or antifungal, such as those described herein. The method may also include combining between approximately 0.1 g and 1.5 g urea. In a further example method, the method includes combining an NSAID agent comprising one or more NSAIDs, such as those described herein. The NSAID may be added in an amount between approximately 0.01 g to approximately 1 g. In a further example of the method, the method comprises combining DMSO. DMSO may be added in a solution to combine with one or more additional components. The DMSO may be added in an amount between approximately 1 g and approximately 10 g. The diluent may be adjusted to obtain a final volume of the topical nail composition between approximately 6 mL and approximately 25 mL. It also be appreciated that the example methods are not limited to an order of combining the various components.

In one example, a method of making a topical nail composition comprises combining an antibacterial agent comprising approximately 1.2 g Tobramycin for Injection, USP and approximately 20 mg mupirocin bulk powder; an antifungal agent comprising approximately 50 mg itraconazole bulk powder; approximately 500 mg urea bulk powder; and a diluent comprising approximately 15 mL 0.09% Sterile Sodium Chloride. In various embodiments, the tobramycin may be replaced or supplemented with voriconazole, colistimethate, or ceftriaxone, such as approximately 200 mg Voriconazole for Injection, approximately 150 mg Colistimethate for Injection, or approximately 500 mg Ceftriaxone for Injection. A method of treating a bacterial or fungal nail infection may comprise applying the composition to an affected nail once daily or as otherwise directed, such as two or more times a day.

In another example, a method of making a topical nail composition comprises combining an antibacterial agent comprising approximately 80 mg gentamicin bulk powder and approximately 20 mg mupirocin bulk powder; an antifungal agent comprising approximately 50 mg itraconazole bulk powder; approximately 500 mg urea; and a diluent comprising approximately 15 mL 0.09% Sterile Sodium Chloride. In various embodiments, the gentamicin may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection. A method of treating a bacterial or fungal nail infection may comprise applying the composition to an affected nail once daily or as otherwise directed, such as two or more times a day.

According to another example, a method of making a topical nail composition comprises combining an antifungal agent comprising approximately 200 mg Voriconazole for Injection; approximately 500 mg urea; and a diluent comprising approximately 15 mL 0.09% Sterile Sodium Chloride. A method of treating a bacterial or fungal nail infection may comprise applying the composition to an affected nail once daily or as otherwise directed, such as two or more times a day. In various embodiments, the voriconazole may be replaced or supplemented with tobramycin, colistimethate, or ceftriaxone, such as approximately 1.2 g Tobramycin for Injection, approximately 150 mg Colistimethate for Injection, or approximately 500 mg Ceftriaxone for Injection.

According to another example, a method of making a topical nail composition comprises combining an antifungal agent comprising approximately 100 mg itraconazole bulk powder; approximately 500 mg urea bulk powder; and a diluent comprising approximately 15 mL 0.09% Sterile Sodium Chloride. A method of treating a bacterial or fungal nail infection may comprise applying the composition to an affected nail once daily or as otherwise directed, such as two or more times a day. In various embodiments, the itraconazole may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

According to another example, a method of making a topical nail composition comprises combining an antibacterial agent comprising approximately 1.2 g Tobramycin for Injection, USP, and approximately 20 mg mupirocin bulk powder; an antifungal agent comprising approximately 50 mg itraconazole bulk powder; approximately 500 mg urea; approximately 10 mL solution comprising approximately 1.5% diclofenac and approximately 45.5% DMSO; and a diluent comprising approximately 15 mL 0.09% Sterile Sodium Chloride. In various embodiments, the tobramycin may be replaced or supplemented with voriconazole, colistimethate, or ceftriaxone, such as approximately 200 mg Voriconazole for Injection, approximately 150 mg Colistimethate for Injection, or approximately 500 mg Ceftriaxone for Injection. In some embodiments, the amount of diluent may be optionally reduced to less than approximately 10 mL, less than approximately 7 mL, less than approximately 5 mL, less than approximately 3 mL, or excluded. For example, the solution of DMSO and NSAID may replace all or a portion of the sodium chloride. A method of treating a bacterial or fungal nail infection may comprise applying the composition to an affected nail once daily or as otherwise directed, such as two or more times a day.

According to another example, a method of making a topical nail composition comprises combining an antibacterial agent comprising approximately 80 mg gentamicin bulk powder and approximately 20 mg mupirocin bulk powder; an antifungal agent comprising approximately 50 mg itraconazole bulk powder; approximately 500 mg urea; approximately 10 mL solution comprising approximately 1.5% diclofenac and approximately 45.5% DMSO; and a diluent comprising approximately 15 mL 0.09% Sterile Sodium Chloride. In various embodiments, the gentamicin may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection. In some embodiments, the amount of diluent may be optionally reduced to less than approximately 10 mL, less than approximately 7 mL, less than approximately 5 mL, less than approximately 3 mL, or excluded. For example, the solution of DMSO and NSAID may replace all or a portion of the sodium chloride. A method of treating a bacterial or fungal nail infection may comprise applying the composition to an affected nail once daily or as otherwise directed, such as two or more times a day. In various embodiments, the gentamicin may be replaced or supplemented with voriconazole, tobramycin for injection, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection.

According to another example, a method of making a topical nail composition comprises combining an antifungal agent comprising approximately 200 mg Voriconazole for Injection; approximately 500 mg urea bulk powder; approximately 10 mL solution comprising approximately 1.5% diclofenac and approximately 45.5% DMSO; and a diluent comprising approximately 15 mL 0.09% Sterile Sodium Chloride. In various embodiments, the voriconazole may be replaced or supplemented with tobramycin, colistimethate, or ceftriaxone, such as approximately 1.2 g Tobramycin for Injection, approximately 150 mg Colistimethate for Injection, or approximately 500 mg Ceftriaxone for Injection. In some embodiments, the amount of diluent may be optionally reduced to less than approximately 10 mL, less than approximately 7 mL, less than approximately 5 mL, less than approximately 3 mL, or excluded. For example, the solution of DMSO and NSAID may replace all or a portion of the sodium chloride. A method of treating a bacterial or fungal nail infection may comprise applying the composition to an affected nail once daily or as otherwise directed, such as two or more times a day. In various embodiments, the voriconazole may be replaced by tobramycin for injection, colistimethate, or ceftriaxone, such as approximately 1.2 g Tobramycin for Injection, approximately 150 mg Colistimethate for Injection, or approximately 500 mg Ceftriaxone for Injection.

According to another example, a method of making a topical nail composition comprises combining an antifungal agent comprising approximately 100 mg itraconazole; approximately 500 mg urea; approximately 10 mL solution comprising approximately 1.5% diclofenac and approximately 45.5% DMSO; and a diluent comprising approximately 15 mL 0.09% Sterile Sodium Chloride. In various embodiments, the itraconazole may be replaced or supplemented with voriconazole, tobramycin, colistimethate, or ceftriaxone, such as approximately 200 mg Voriconazole for Injection, approximately 1.2 g Tobramycin for Injection, approximately 150 mg Colistimethate for Injection, or approximately 500 mg Ceftriaxone for Injection. In some embodiments, the amount of diluent may be optionally reduced to less than approximately 10 mL, less than approximately 7 mL, less than approximately 5 mL, less than approximately 3 mL, or excluded. For example, the solution of DMSO and NSAID may replace all or a portion of the sodium chloride. A method of treating a bacterial or fungal nail infection may comprise applying the composition to an affected nail once daily or as otherwise directed, such as two or more times a day.

Methods of Treating a Bacterial or Fungal Nail Infection

A method of treating a bacterial or fungal nail infection may include topically applying any topical nail composition disclosed herein. For example a topical nail composition may be directly applied to an affected nail surface. In some embodiments, topical administration to the affected nail surface may include layering or coating the nail surface with the topical nail composition. The topical nail composition may be applied directly to the nail surface via a brush, sponge, dropper, syringe, or other applicator. In one example, the topical nail composition may be painted onto the nail surface. The topical nail composition may be administered 1 to 4 times daily or as otherwise directed to treat the nail infection.

According to one embodiment, a method of pretreating a bacterial or fungal nail infection may include applying a solution containing a NSAID and DMSO to a nail before applying the topical nail composition to the nail. The solution containing the NSAID and DMSO may be as described herein. For example, the solution may include one or more NSAIDS selected from oxicams, such as meloxicam and piroxicam; salicylic acid derivatives, such as aspirin, diflunisal, salsalate, and trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, and tolmetin; fenamates, such as meclofenamate; and/or COX-2 inhibitors, such as celecoxib, rofecoxib, and valdecoxib. In one embodiment, the NSAID includes diclofenac. Diclofenac may be present in an amount between approximately 0.05% and approximately 5%, such as between approximately 1% and approximately 3%, between approximately 1% and approximately 2%, or approximately 1.5%. DMSO may be present in an amount between approximately 10% and approximately 50%, such as between approximately 15% and approximately 50%, between approximately 20% and approximately 50%, between approximately 25% and approximately 50%, between approximately 30% and approximately 50%, between approximately 35% and approximately 50%, between approximately 40% and approximately 50%, or between approximately 20% and approximately 40%.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x". "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of treating a bacterial nail infection, comprising:
   mixing ceftriaxone and a sodium chloride solution to formulate a topical nail composition, wherein the topical nail composition is an aqueous solution or suspension;
   pre-treating a nail prior to applying the topical nail composition to the nail, wherein pre-treating the nail comprises topically applying a pre-treatment solution containing a NSAID and DMSO to the nail, and
   topically applying the topical nail composition directly to the nail affected by a bacterial infection to treat the bacterial infection of the nail.

2. The method of claim wherein mixing the ceftriaxone and the sodium chloride solution comprises mixing the sodium chloride solution with Ceftriaxone for Injection.

3. The method of claim 2. wherein the topical nail composition comprises approximately 1% to approximately 10% ceftriaxone by weight.

4. (The method of claim 1, wherein the method further comprises mixing urea with the sodium chloride solution and ceftriaxone.

5. The method of claim 4, wherein the urea is mixed in an amount to obtain between 1% and 30% urea by weight of the topical nail composition.

6. The method of claim 5, wherein the ceftriaxone is mixed with the sodium chloride solution in an amount wherein the topical nail composition comprises between approximately 1% to approximately 10% ceftriaxone by weight.

7. The method of claim 6, wherein the DMSO is present in an amount between 25% and 50% by weight of the pre-treatment solution, wherein the NSAM comprises diclofenac, and wherein the diclofenac is present in au amount between 0.05% and 5% by weight of the pre-treatment solution.

8. The method of claim 5, wherein mixing the ceftriaxone and the sodium chloride solution comprises mixing ceftriaxone for Injection with the sodium chloride solution in an amount wherein the topical nail composition comprises approximately 1% to approximately 10% ceftiriaxone by weight.

9. The method of claim 1., further comprising mixing at least one additional active agent to formulate the topical nail composition selected from an antibiotic, antifungal, or NSAID.

10. The method of claim 1, wherein the NSAID in the pre-treatment solution is diclofenac.

11. The method of claim 10, wherein the cefiriaxone is mixed with the sodium chloride solution in an amount wherein the topical nail composition comprises approximately 1% to approximately 10% ceftriaxone by weight.

12. The method of claim 11, further comprising mixing urea, wherein the urea is mixed with the ceftriaxone and sodium chloride solution in an amount wherein the topical nail. composition comprises between 1% and 20% urea by weight, and wherein the pre-treatment solution comprises between 25% and 50% DMSO and between 0.05% and 5% diclofenac by weight.

13. The method of claim 1, wherein the DMSO is present in an amount between 25% and 50% by weight of the pre-treatment solution, wherein the NSAID comprises diclofenac, and wherein the diclofenac is present in an amount between 0.05% and 5% by weight of the pre-treatment solution.

14. A method of treating a bacterial nail infection, the method comprising:
    pre-treating a nail prior to applying a topical nail composition to the nail, wherein pre-treating the nail comprises topically applying a pre-treatment solution containing a NSAID and DMSO to the nail,
    topically applying a topical nail composition directly to the nail affected by a bacterial infection to treat the bacterial infection of the nail, and
    wherein the topical nail composition comprises an aqueous solution or suspension comprising between 1% and 10% ceftriaxone by weight and a sodium chloride solution.

15. The method of claim 14, wherein the topical nail composition further comprises between 1% and 30% urea by weight.

16. The method of claim 15, wherein the NSAID is diclofenac and comprises between 1% and 3% diclofenac by weight of the pre-treatment composition.

17. The method of claim 14, wherein the DMSO is present in an. amount between 25% and 50% by weight of the pre-treatment solution, wherein the NSAID comprises diclofenac, and wherein the diclofenac is present in an amount between 0.05% and 5% by weight of the pre-treatment solution.

* * * * *